(12) United States Patent
Parry et al.

(10) Patent No.: US 7,931,656 B2
(45) Date of Patent: Apr. 26, 2011

(54) ACETABULAR SHELL IMPACTOR

(75) Inventors: Douglas S. Parry, Sandy, UT (US);
Scott R. Parry, Draper, UT (US)

(73) Assignee: Paramount Medical Instruments, L.L.C., Sandy, UT (US)

( * ) Notice: Subject to any disclaimer, the term of this patent is extended or adjusted under 35 U.S.C. 154(b) by 777 days.

(21) Appl. No.: 10/838,152

(22) Filed: Apr. 30, 2004

(65) Prior Publication Data
US 2005/0203535 A1    Sep. 15, 2005

Related U.S. Application Data

(60) Provisional application No. 60/534,431, filed on Jan. 5, 2004, provisional application No. 60/541,344, filed on Feb. 2, 2004.

(51) Int. Cl.
*A61B 17/58* (2006.01)
(52) U.S. Cl. .......................................... 606/91
(58) Field of Classification Search .................. 606/91, 606/80, 81, 86 R, 89, 99, 100
See application file for complete search history.

(56) References Cited

U.S. PATENT DOCUMENTS

| | | | |
|---|---|---|---|
| 3,859,992 A * | 1/1975 | Amstutz | 606/91 |
| 4,305,394 A | 12/1981 | Bertuch, Jr. | |
| 4,517,977 A * | 5/1985 | Frost | 606/170 |
| 4,632,111 A | 12/1986 | Roche | |
| 4,795,469 A | 1/1989 | Oh | |
| 5,061,270 A | 10/1991 | Aboczky | |
| 5,116,339 A | 5/1992 | Glock | |
| 5,156,626 A | 10/1992 | Broderick et al. | |
| 5,431,657 A | 7/1995 | Rohr | |
| 5,474,560 A | 12/1995 | Rohr, Jr. | |
| 5,766,260 A | 6/1998 | Whiteside | |
| 5,954,727 A | 9/1999 | Collazo | |
| 6,086,587 A | 7/2000 | Hawk | |
| 6,132,470 A | 10/2000 | Berman | |
| 6,152,930 A * | 11/2000 | Mastrorio | 606/99 |
| 6,558,314 B1 * | 5/2003 | Adelman et al. | 600/37 |
| 2002/0116007 A1 | 8/2002 | Lewis | |
| 2002/0183851 A1 | 12/2002 | Spiegelberg et al. | |

(Continued)

FOREIGN PATENT DOCUMENTS

| | | |
|---|---|---|
| FR | 1.041.311 | 5/1953 |
| WO | WO/03/065906 A2 | 2/2003 |

OTHER PUBLICATIONS

Wright Medical Technology, Inc. "Lineage® acetabular cup system" product literature, 2002.

(Continued)

*Primary Examiner* — Eduardo C Robert
*Assistant Examiner* — Tara R Carter
(74) *Attorney, Agent, or Firm* — Clayton, Howarth & Cannon, P.C.

(57) ABSTRACT

A method and apparatus for implanting acetabular components into an acetabulum utilizing a minimally invasive incision. The method and apparatus utilize a subatmospheric pressure formed in a hollow passage of an elongate body to secure an acetabular shell to a shell-engaging head removably attached to a coupler end of the elongate body. Liner-engaging heads may also be removably attached to the coupler end to install socket liners into an implanted acetabular shell. The elongate body may comprise a bent portion to allow access to the acetabulum through a minimally invasive incision.

43 Claims, 10 Drawing Sheets

U.S. PATENT DOCUMENTS

| | | | |
|---|---|---|---|
| 2003/0050645 A1* | 3/2003 | Parker et al. ................... | 606/99 |
| 2003/0125810 A1 | 7/2003 | Sullivan et al. | |
| 2003/0220647 A1* | 11/2003 | McCallum et al. ............. | 606/81 |
| 2003/0229356 A1 | 12/2003 | Dye | |

OTHER PUBLICATIONS

Wright Medical Technology, Inc. "Conserve® Total Hip System with BFH™ Technology" product literature, 2003.

Zimmer "Minimally Invasive Hip Instruments: Optimizing exposure and preserving soft tissue during THA," 2003.

Wright Medical Technology, Inc. "Lineage™ Acetabular Cup System: Performance characteristics of the Ceramic Lineage™ Articulation System," 2001.

Wright Medical Technology, Inc. "Perfecta® Total Hip System" product literature, 1998.

\* cited by examiner

ACETABULAR SHELL IMPACTOR

CROSS-REFERENCE TO RELATED APPLICATIONS

This application claims the benefit of U.S. Provisional Application No. 60/534,431, filed Jan. 5, 2004, and U.S. Provisional Application No. 60/541,344, filed Feb. 2, 2004, which applications are hereby incorporated by reference herein in their entireties, including but not limited to those portions that specifically appear hereinafter, the incorporation by reference being made with the following exception: In the event that any portion of the above-referenced provisional applications is inconsistent with this application, this application supercedes said above-referenced provisional applications.

STATEMENT REGARDING FEDERALLY SPONSORED RESEARCH OR DEVELOPMENT

Not Applicable.

BACKGROUND

1. The Field of the Invention

The present disclosure relates generally to surgical instruments, and more particularly, but not necessarily entirely, to an apparatus and method for implanting surgical prostheses during surgery.

2. Description of Related Art

The number of total hip replacement surgeries has increased dramatically in recent years. Hip replacement surgery involves implanting a prosthesis to replace an ailing hip joint. The prosthesis is typically made up of two parts: an acetabulum component, or socket portion, which replaces the acetabulum and a femoral component, which replaces the femoral head. The acetabulum component may in turn comprise a metal shell, hereinafter referred to as an acetabular shell, with a plastic or ceramic inner socket liner, hereinafter referred to as a socket liner.

The steps for replacing the hip begin with the surgeon making an incision over the hip joint. There are several different approaches used to make the incision, usually based on the surgeon's training and preferences. After the incision is made, the ligaments and muscles may be separated to allow the surgeon access to the bones of the hip joint. Once the hip joint is entered, the femoral head may be dislocated from the acetabulum. Then the femoral head may be removed by cutting through the femoral neck with a saw. After the femoral head is removed, the cartilage may be removed from the acetabulum using a power drill and a special reamer. The reamer may be used to form the bone in a hemispherical shape to exactly fit the acetabular shell of the acetabular component. Once the right size and shape is determined for the acetabulum, the acetabular shell may be inserted into place. In the uncemented variety of artificial hip replacement, the acetabular shell may be simply held in place by the tightness of the fit or with screws to hold the metal shell in place. Insertion of the acetabular shell may be done by hand or by use of a hand tool that grips the shell. Often, the surgeon may set the acetabular shell into the acetabulum by impacting it through the use of a mallet and an impaction device. The surgeon may then insert a socket liner into the acetabular shell. Once the acetabular shell and socket liner are in place, the surgeon may then replace the femoral head with a femoral component and the surgeon may reassemble the hip joint. The surgeon may also test the movement of the hip joint before closing the incision.

One of the major difficulties confronting the surgeon during hip replacement surgery is the relatively inaccessible location of the acetabulum making it difficult for the surgeon to correctly position the acetabular components. In the past, the solution has been to make a relatively large incision to allow the surgeon complete and unfettered access to the hip joint. However, from the patient's perspective, a large incision is undesirable as it increases the trauma to the patient and the recovery time.

Attempts have been made in the previously available devices to provide a hand tool to assist in holding and positioning an acetabular shell. U.S. Pat. No. 5,116,339 (granted May 26, 1992 to Glock) discloses an installation tool having an expanding head for engaging the acetabular shell. The acetabular shell is released by contracting the head when the shell is in position. The head is expanded and contracted by means of a threaded shaft with a knob such that rotation of the knob correspondingly expands or contracts the head. U.S. Pat. No. 4,305,394 (granted on Dec. 15, 1981 to Bertuch) discloses an acetabular shell positioning device comprising an interchangeable ball and flange for engaging the inner cavity of the acetabular shell by a mechanical engagement. A coupling rod with a handle is manipulated in order to engage and release the acetabular shell.

U.S. Pat. No. 3,859,992 (granted on Jan. 14, 1975 to Amstutz) discloses a suction-operated holding and positioning instrument for use in inserting an acetabular shell during hip surgery. The Amstutz device includes a permanently affixed shell-engaging head and an external suction source for forming a suction force between the shell-engaging head and the shell. The Amstutz device further provides a port controlled by a mechanical valve for selectively breaking the suction force formed between the shell-engaging head and the shell. The Amstutz device does not appear to be able to be used with cementless acetabular shells that require impaction.

The above devices are characterized by several disadvantages including complicated designs involving several moving parts that both increase manufacturing costs as well as making the device more difficult to use during an operation. In particular, the Amstutz device disadvantageously requires a connection to an external suction source. The Amstutz device further does not allow for interchangeable shell-engaging heads to allow the device to be used with different sized acetabular shells. Finally, it appears that none of the above devices can be used to both implant an acetabular shell and a socket liner.

In addition, the shape of the devices dictate the use of relatively large incisions during surgery. One attempted improvement over the previously available devices to reduce the size of the required incision is disclosed in U.S. Patent Publication Application 2003/0229356 (published Dec. 11, 2003 to Dye). The Dye apparatus includes a curved impaction instrument for aligning and impacting the acetabular component into the acetabulum. The curved shape of the apparatus allows for a minimally invasive incision in the patient.

Similarly, U.S. Patent Publication Application 2003/0050645 (published Mar. 13, 2003 to Parker et al.) discloses a curved impactor having a hollow outer shaft and a flexible drive shaft disposed in the outer shaft. The flexible drive shaft is connected at one end to a coupler, and at the opposite end is a thumb wheel, such that rotation of the thumb wheel rotates the drive shaft and engages the coupler to an acetabular shell.

Unfortunately, despite their advantages, both the Dye and Parker et al. apparatuses still has several shortcomings. In particular, the attachment of the acetabular shell to the device requires a mechanical engagement of the shell to the device. Dye is particularly disadvantageous due to the fact that it does not teach a remote release of the acetabular shell once it is installed in the acetabulum. Parker et al., on the other hand, is disadvantageous due to its overly complicated remote release mechanism.

The prior art is thus characterized by several disadvantages that are addressed by the present disclosure. The present disclosure minimizes, and in some aspects eliminates, the above-mentioned failures, and other problems, by utilizing the methods and structural features described herein. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which:

FIG. 2A is a cross-sectional, break-away view of an alternative embodiment of the impactor of FIG. 2.

DETAILED DESCRIPTION

Figure 1:
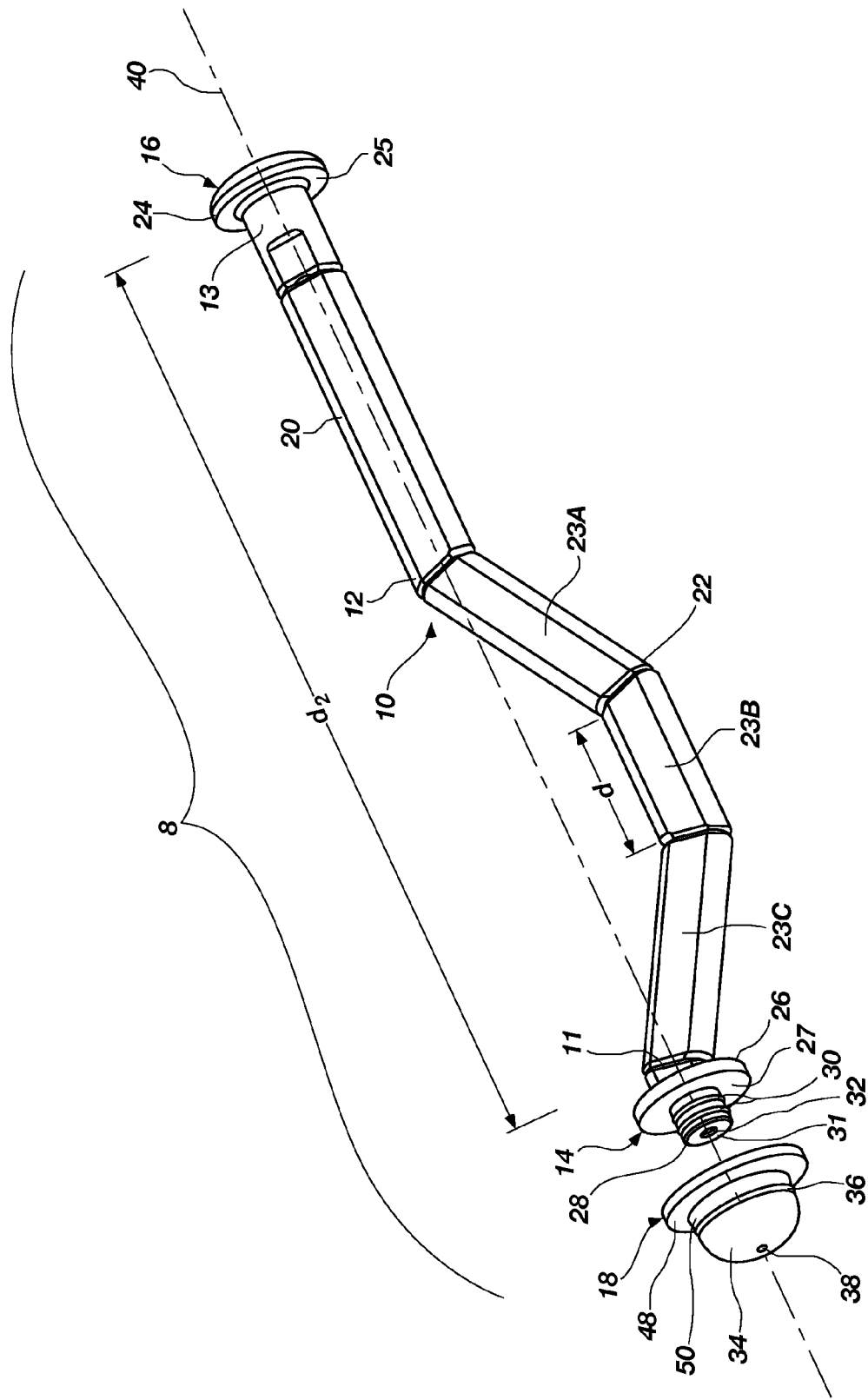
FIG. 1 is an exploded perspective view of one exemplary embodiment made in accordance with the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It is also to be understood that the terminology employed herein is used for the purpose of describing particular embodiments only and is not intended to be limiting since the scope of the present disclosure will be limited only by the appended claims and equivalents thereof.

It must be noted that, as used in this specification and the appended claims, the singular forms "a," "an," and "the" include plural referents unless the context clearly dictates otherwise. In describing and claiming the present disclosure, the following terminology will be used in accordance with the definitions set out below. As used herein, the terms "comprising," "including," "containing," "characterized by," and grammatical equivalents thereof are inclusive or open-ended terms that do not exclude additional, unrecited elements or method steps.

Applicant has discovered a simple and easy to use apparatus for positioning and implanting an acetabular shell into the a patient's acetabulum during hip replacement surgery using minimally invasive surgical techniques. Applicant's disclosure may also be utilized to implant a socket liner in an implanted acetabular shell. Importantly, Applicant's disclosure does not require a mechanical engagement means to engage and hold the acetabular shell during implantation. Instead, Applicant's disclosure teaches the use of subatmospheric pressure to hold the acetabular shell on an engaging head. One aspect of the disclosure is unique in that an external suction source may not be required in order to create the subatmospheric pressure. Applicant's disclosure may also comprise a valveless and open port sealable by a finger for allowing the subatmospheric pressure to be created and to be broken, to thereby selectably release the acetabular shell from an engaging head. In addition, another aspect of the Applicant's disclosure may permit the use of interchangeable engaging heads thereby permitting the implantation of acetabular shells and socket liners of different sizes with the same apparatus.

As used herein, the term "minimally invasive incision" means an incision as is known in the art to reduce trauma in the patient, for example an incision ranging between about two and one-half inches and about five and one-half inches. As used herein, the term "pressure-maintaining seal" means a seal that inhibits airflow to a degree sufficient to enable a non-atmospheric pressure to be established and maintained at a non-atmospheric level, whether the non-atmospheric pressure is constant or varies within a non-atmospheric range.

Referring now to FIG. 1, reference numeral 8 generally refers to an acetabular shell impactor assembly pursuant to one embodiment of the Applicant's disclosure. The assembly 8 may comprise an impactor 10 and a tool or engaging head, such as a shell-engaging head 18, disposed on the impactor 10. The impactor 10 may comprise an elongate body 12 extending from a distal end 11 to a proximal end 13. A coupler end 14 and a head 16 may be disposed on the distal end 11 and the proximal end 13, respectively. The elongate body 12 may have a hollow passage 54 in its interior extending between the coupler end 14 and the head 16 as can best be seen in FIG. 2, and said hollow passage 54 may be closeable.

Referring back to FIG. 1, the elongate body 12 may further comprise a first portion 20 extending from the proximal end 13 along a longitudinal axis 40 towards the coupler end 14.

The first portion 20 may be substantially straight and may be used as a handle by a surgeon during surgery to assist in positioning the impactor 10. In particular, a surgeon grasping the handle near the proximal end 13 may be able to place the thumb of the hand grasping the handle over the port 42 located on the top surface 17 of the head 16, in order to seal the port 42 with a pressure-maintaining seal and thereby close the hollow passage 54 when an implant such as shell 62 is disposed on the engaging head 18.

A second portion 22 of the elongate body 12 may extend between the first portion 20 and the coupler end 14. The second portion 22 may form a bend in the elongate body 12 such that the second portion 22 may, if desired, deviate from and return to the longitudinal axis 40. The second portion 22 may comprise a first segment 23A, a second segment 23B, and a third segment 23C as shown in FIG. 1. The first segment 23A may be connected to the first portion 20 at an angle such that the first segment 23A departs from the longitudinal axis 40. The second segment 23B may be connected to the first segment 23A. The second segment 23B may be substantially parallel to the longitudinal axis 40. The third segment 23C may be connected to the second segment 23B at an angle such that the third segment 23C is directed back towards the longitudinal axis 40 in the direction of the coupler end 14. In one embodiment of the present disclosure, the second segment 23B may extend substantially parallel to the longitudinal axis 40 a distance d, that may be at least 10 percent of a distance d2 extending between the proximal end 13 and the distal end 11 of the impactor 10 along the longitudinal axis 40, as shown in FIG. 1.

The bend in the second portion 22 may be sized and shaped such that the coupler end 14 can be positioned inside of the patient while the head 16 is positioned outside of the patient. It will be appreciated by those skilled in the art that the bend in the second portion 22 may allow an acetabular shell to be positioned and impacted into a reamed acetabulum through a minimally invasive incision. Further, the bend in the second portion allows the impactor 10 to be positioned so as not to interfere with other anatomical structures around the acetabulum while the acetabular shell is brought into and implanted into the acetabulum. Further, the bend may allow an almost linear transfer of an impaction force from the head 16 to an acetabular shell along the longitudinal axis 40 without disturbing the surrounding anatomical structures.

In will be appreciated that the bend may be located on the impactor 10 at different locations along the elongate body 12 to facilitate varying surgical techniques. Further, the bend may be curved, elliptical, piecewise linear, or circular in shape with a constant or varying curvature. In this regard, it will be appreciated that the second portion 22 may have alternative embodiments other than then bend as described above. For example, the second portion 22 may be curved, arced or circular. In some embodiments, the second portion 22 may even be straight. It should also be noted that the elongate body 12 may be of modular or one piece construction. The modular construction may include a combination of linear or non-linear segments. It will be understood that the bend and the elongate body 12 may constitute a means for positioning an acetabular shell into an acetabulum through a minimally invasive incision.

As mentioned, the head 16 may be disposed on the proximal end 13 of the elongate body 12. As can best be seen in FIG. 3, the head 16 may comprise a top surface 17 that may be planar, and an annular rim 24. The top surface 17 may be of sufficient size to receive an impaction force from a surgical mallet or the like. The annular rim 24 may protect the hand of the surgeon holding the impactor 10 from missed or glancing blows from the surgical mallet.

Figure 2:
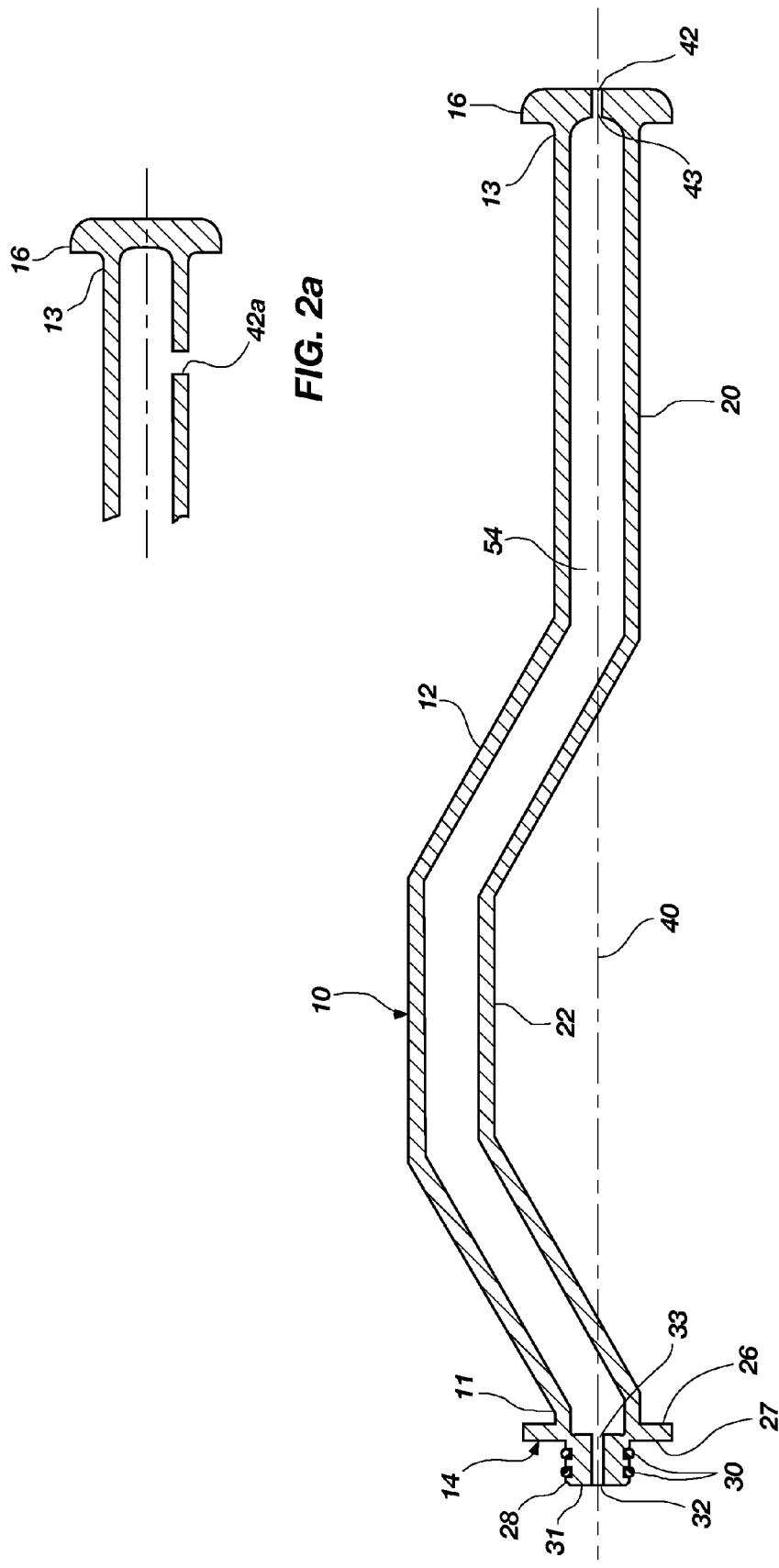
FIG. 2 is a cross-sectional view of one exemplary embodiment of an impactor.
Figure 3:
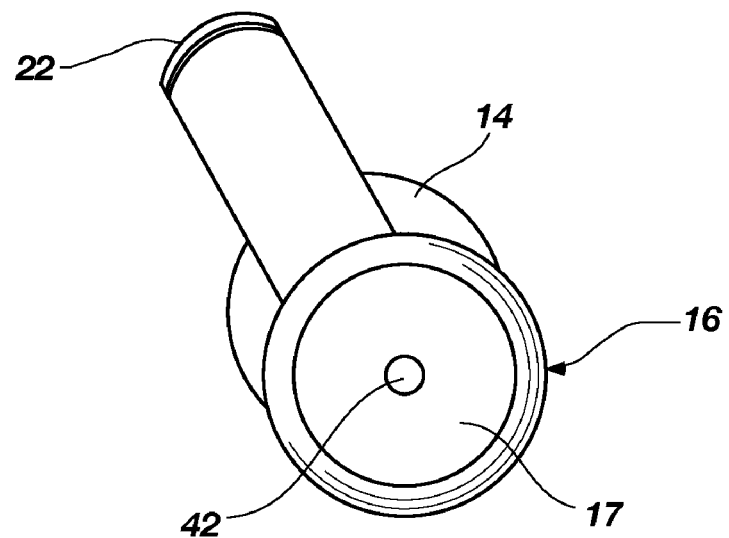
FIG. 3 is an end view of the impactor illustrated in FIG. 2 made in accordance with the present disclosure.
Figure 4C:
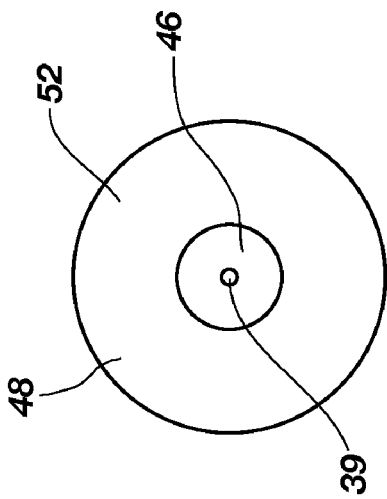
FIG. 4C is a bottom view of an exemplary engaging head made in accordance with the present disclosure.
Figure 4B:
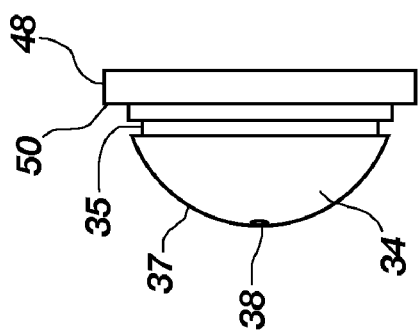
FIG. 4B is a side view of an exemplary engaging head made in accordance with the present disclosure.
Figure 4A:
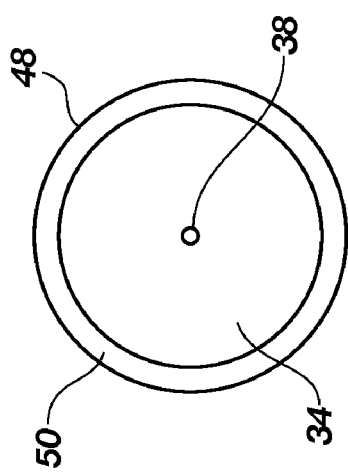
FIG. 4A is a top view of an exemplary engaging head made in accordance with the present disclosure.

In addition, in the center of the top surface 17 may be a port 42 as viewed in FIG. 3. The port 42 may be in fluid communication with the hollow passage 54 in the elongate body 12 as is best shown in FIG. 2. The port 42 may be sized and positioned in the top surface 17 such that a thumb can placed over the port 42 to thereby create a pressure-maintaining seal. The port 42 may be situated along the longitudinal axis 40. It should be noted, that it is within the scope of this disclosure that the position of the port 42 may be located anywhere on the head 16 or the elongate body 12. For example, in reference to FIG. 2A, it will be appreciated that a port 42a may be formed to extend through the elongate body 12 in a radial direction, in lieu of port 42 in FIG. 2.

The port 42 may be valveless and open. As used herein, the term "open" means in fluid communication with the atmosphere such that the atmosphere may enter the hollow passage 54 through the port 42 when the port 42 is not sealed. Moreover, while it is less desirable, a mechanical valve as is known in the art may be used to operate and seal the port 42, but typically the port 42 may be sealed with the thumb of a surgeon as described above. It will be understood that the port 42 may constitute a means for selectively breaking a subatmospheric pressure in the hollow passage 54.

Figure 7:
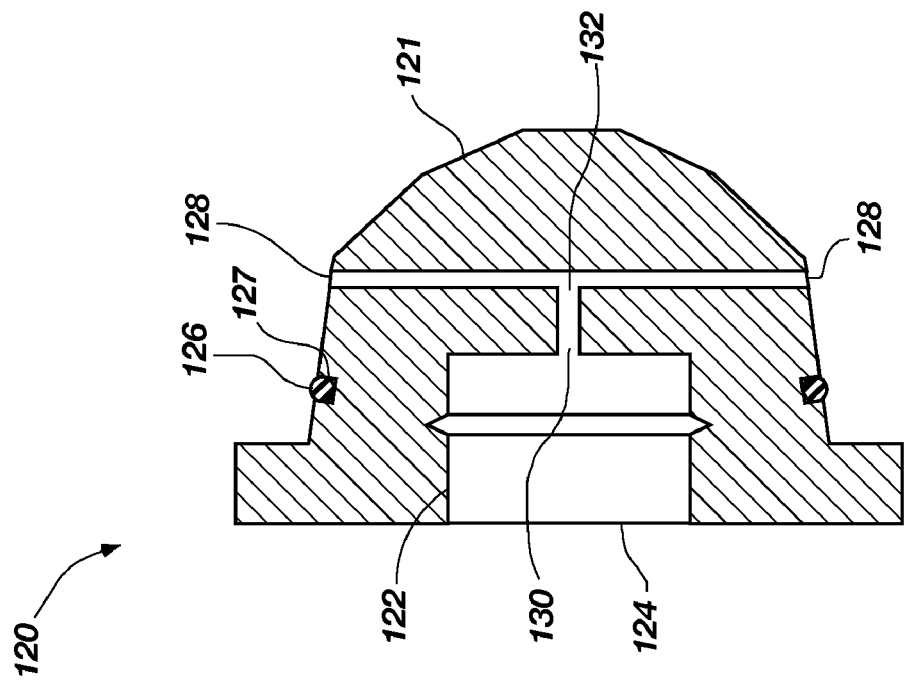
FIG. 7 is a cross-sectional side view of still another embodiment of an engaging head made in accordance with the present disclosure.

The coupler end 14 of the impactor 10 as shown in FIG. 1 may be utilized to removably and interchangeably attach the engaging head capable of engaging a surgical implant, such as a shell-engaging head 18 or a socket-liner-engaging head 58 (see FIGS. 7 and 8). The coupler end 14 may comprise an annular flange 26 extending radially from the longitudinal axis 40. The side of the annular flange 26 facing away from the distal end 11 may form a seat 27 against which an engaging head may be oriented.

Extending from the middle of the seat 27 along the longitudinal axis 40 and in a direction away from the distal end 11 may be an extension member 28. The extension member 28 may extend in a substantially perpendicularly direction from the seat 27 and may be substantially cylindrical in shape but it will be appreciated by those skilled in the art that other shapes may be permissible that are consistent with the present disclosure.

The extension member 28 may comprise an outer surface having a forward-most annular groove and a rear-most annular groove each of which are adapted to receive a resilient member 30, such as an o-ring. An exposed end 31 of the extension member 28 may have a port 32 located thereon in fluid communication with hollow passage 54 in the elongate body 12 as may be observed best in FIG. 2. The port 32 may be centered on or off of the longitudinal axis 40.

As will be discussed in more detail below, the extension member 28 may be sized and shaped to slidably and removably engage an engaging head, such as a shell-engaging head 18 or a socket-liner-engaging head 58 (see FIGS. 7 and 8), by a pressure-maintaining seal. It should be noted, however, that other methods of attaching an engaging head to the coupler end 14 are known to those skilled in the art that fall within the scope of this disclosure. For example, an engaging head may rotatably engage the coupler end 14. Also, an engaging head may be permanently mounted onto the coupler end 14. Alternatively, the engaging head and the impactor 10 may be constructed as a one-piece unitary member. Moreover, with respect to the resilient members 30, a pressure-maintaining seal may be formed by using either a single resilient member 30, or a pair of resilient members 30 as shown most clearly in FIG. 2, or some other plurality of resilient members 30, may be positioned in a variety of locations either on the engaging head or the coupler end 14 as is known in the art to facilitate the formation of a pressure-maintaining seal between the coupler end 14 and the engaging head. Further, it will be appreciated that the resilient members 30 may not be required at all for achieving the pressure-maintaining seal. It will be understood that the coupler end 14 may constitute a means for selectively engaging any one of a plurality of engaging heads by a pressure-maintaining seal.

A cross-sectional view of the impactor 10 is shown in FIG. 2. As previously mentioned, the hollow passage 54 extends from the distal end 11 to the proximal end 13 of the elongate body 12 through both the first portion 20 and the second portion 22. Port 42 may be positioned in the top surface 17 of the head 16 and may be interconnected with the hollow passage 54 by a fluid communication path 43. Likewise, port 32 may be positioned in the exposed end 31 and may be interconnected with the hollow passage 54 by a fluid communication path 33. In addition, port 42 and port 32 may constitute the only egresses from the hollow passage 54. It will be observed, that both port 42 and port 32, as well as fluid communication paths 33 and 43 may lie on the longitudinal axis 40.

The size of the ports 42 and 32 may be smaller than that of the hollow passage 54. As explained above, port 42 may be configured and sized such that it may be sealed by a thumb of a surgeon. As will be explained in greater detail below, port 32 may be configured and sized to align with a fluid communication path in an engaging head. Typically, fluid communication path 43 is through the head 16 while fluid communication path 33 is through the coupler end 14. It will be appreciated, however, that it is a feature of this disclosure that the ports 42 and 32 may be positioned anywhere along the impactor 10. It will be understood that the hollow passage 54 may constitute a means for forming a subatmospheric pressure.

Annular flange 26 may extend radially from the longitudinal axis 40 while extended member 28 may extend parallel and along the axis 40 away from the distal end 11. Seat 27 and exposed end 31 may be perpendicular to the longitudinal axis 40. Resilient members 30 on the extended member 28 may be radially positioned from the axis 40.

FIGS. 1, 4A, 4B, and 4C show an isometric view, a top view, side view and a bottom view, respectively, of one embodiment of the shell-engaging head 18 which, as mentioned above, may be removably attachable to the coupler end 14 of the impactor 10. The shell-engaging head 18 may comprise a base portion 48 and a tip portion 34 extending from a surface 50 of the base portion 48. The tip portion 34 may be substantially partially spherical, such as a substantially hemispherical. The tip portion 34 may extend such that is substantially centered on the surface 50 of the base portion 48.

The tip portion 34 may further comprise an annular groove 35 on its outer surface 37 that may be adapted to receive a resilient member 36 (not shown in FIG. 4A, 4B or 4C), such as an o-ring. A port 38 may be positioned in the outer surface 37. Located in a rearmost portion 52 of the base portion 48 may be a recessed portion 46 having a port 39 in fluid communication with port 38 on the outer surface 37.

Figure 5:
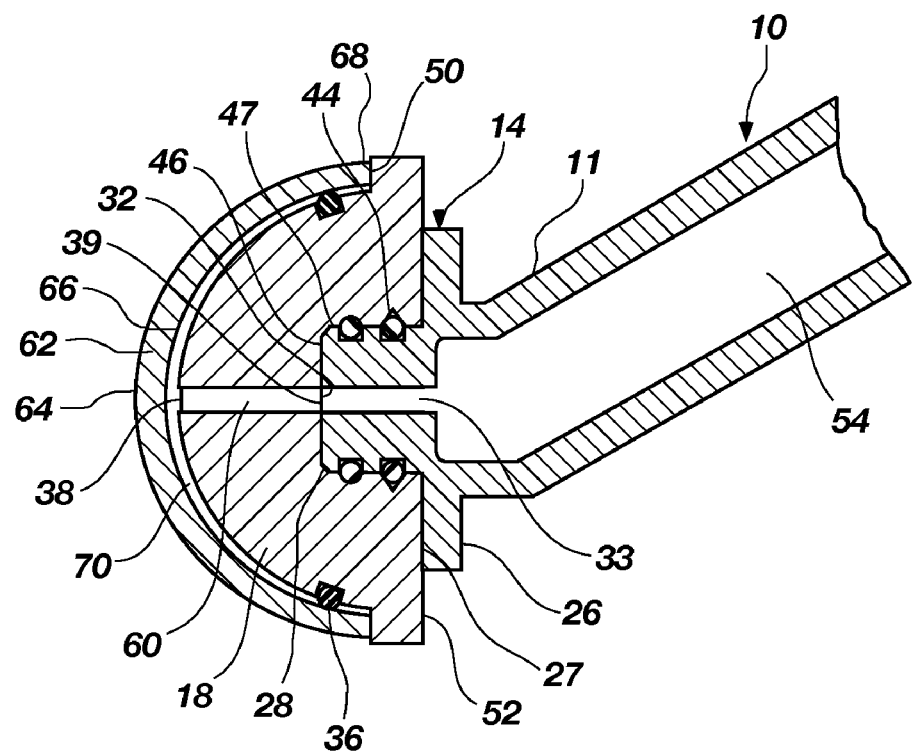
FIG. 5 is a cross-sectional side view of the impactor, shell-engaging head and an acetabular shell made in accordance with the present disclosure.

Looking now to a cross-sectional view of the engagement of the engaging member 18 and the coupler end 14, the recessed portion 46 may slidably engage the extended member 28 as shown in FIG. 5. The rearmost of the resilient members 30 on the extension member 28 may engage an annular locking grove 44 formed in a side wall 47 of the recessed portion 46 in order to form a friction fit to hold the engaging member 18 on the coupler end 14. The frontmost resilient member 30 on the extension member 28 may also engage the side wall 47 of the recessed portion 46 which may provide an additional seal as well as a friction fit to hold the engaging head onto the coupler end 14. It will be appreciated that the engagement between the rearmost of the resilient members 30 and the locking groove 44 may also form a pressure-maintaining seal.

The rearmost portion 52 of the base portion 48 may abut directly against the seat 27 of the annular flange 26 when the shell-engaging head 18 is installed on the coupler end 14. This interaction may serve to properly orient the shell-engaging head 18. Likewise, the exposed end 31 of the extension member 28 may abut against a bottom portion 56 of the recessed portion 48.

It will be observed that when the shell-engaging head 18 is properly installed onto the coupler end 14, that port 32 is in alignment and adjacent with port 39 such that port 38 is in direct fluid communication with the hollow passage 54. In this regard, the fluid communication path 33 may be interconnected with a fluid communication path 60 extending from port 38 to port 39.

In the above described arrangement, the shell-engaging head 18 may be removed from the impactor 10 by using sufficient force to pull it off. It will be appreciated that the force to pull off the shell-engaging head 18 should be such that it can be done by an average strength human being as it may be necessary during surgery to replace the shell-engaging head 18.

It will also be noted that an engaging head may be disposed on the elongate body in a modular or integral manner. It will be appreciated that if the engaging head is disposed on the elongate body in an integral manner, that a coupler end 14 is not needed and the engaging head may be disposed directly on the distal end 11. Alternatively, modular embodiments of the engaging head may have an intervening structure, such as the coupler end 14, between the engaging head and the distal end 11. It is to understood that the phrase "disposed on," when used in reference to the engaging head being disposed on an object (such as the distal end of the elongate body 12), means that the engaging head is held in relation to said object either in a modular or integral manner, either directly or indirectly. Referring now specially to FIG. 5, the forgoing definition of the engaging head being "disposed on" an object, includes the concept that the engaging head 18 is disposed on the distal end 11 of the elongate member 12, because said engaging head 18 is held in relation to said distal end 11, even though engaging head 18 and distal end 11 are not in any contact, but are intercoupled by the coupler end 14.

FIG. 5 also illustrates the engagement of an acetabular shell 62 having an outer surface 64 and an inner surface 66 with the shell-engaging head 18. A rearmost portion 68 of the shell 62 may abut against the surface 50 of the shell-engaging head 18 when the tip portion 34 is inserted into shell 62. Resilient member 36 disposed in groove 35 on the outer surface 37 may form a pressure-maintaining seal with the inner surface 66 of the shell 62. An enclosed region 70 may be defined by the inner surface 66 and the outer surface 37. The enclosed region 70 may be in fluid communication with the hollow passage 54 and may be substantially airtight.

Figure 6:
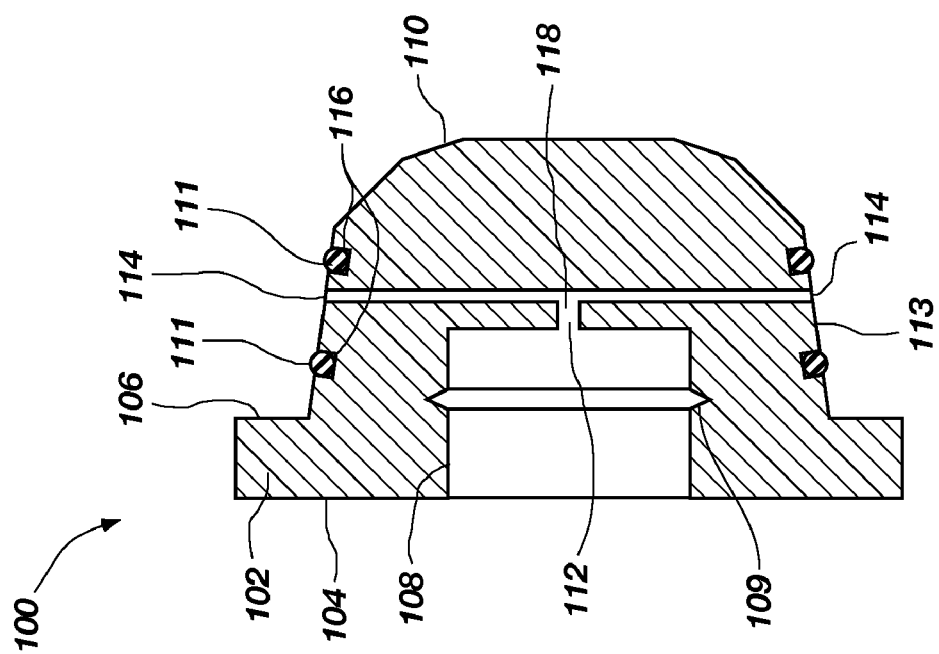
FIG. 6 is a cross-sectional side view of another embodiment of an engaging head made in accordance with the present disclosure.

FIGS. 6 and 7 illustrate alternative embodiments of engaging heads indicated by reference numerals 100 and 120, respectively. In FIG. 6, the engaging head 100 may comprise a base portion 102 having a surface 106 and a rearmost portion 104. A tip portion 110 may extend from the surface 106. The tip portion 110 may comprise at least one frusto-conical portion 113 having two resilient members 111 disposed in annular grooves 116 for forming a substantially airtight enclosed region with an inner portion of an acetabular shell. It will be appreciated that the enclosed region may be between the two resilient members 111. Ports 114 may be positioned between the two resilient members 111 and be fluidly connected by a fluid communication path 118 to a port 112 located within a recessed portion 108. As before, the recessed portion 108 may have a locking groove 109 to engage the extension member 28 of the coupler end 14 as was described above and is incorporated here by reference.

FIG. 7, illustrates an engaging head 120 that may be similar to that in FIG. 6, except that there may be only a single resilient member 126 in an annular groove 127 formed in the tip portion 121. Ports 128 may be fluidly connected to port 130 in the recessed portion 122 by a fluid communication path 132.

In will be appreciated that embodiments of engaging heads may include various configurations all of which fall within the scope of the present disclosure. Some of these various configurations may include, without limitation, some of the following features in any combination: a tip portion having one, two or three resilient members in its outer surface, one, two or three ports in the recessed portion in fluid communication, either individually or in combination, with one, two or three ports in the outer surface, one, two or three ports located in the outer surface disposed at any location on the tip portion, and a tip portion having a partially spherical shape, substantially hemispherical shape, a shape having one or more frustoconical portions, or any random shape fitting with a inner portion of an acetabular shell or implant.

It will be appreciated that the various embodiments of the engaging head enable the Applicant's disclosure to be utilized with the numerous variations in the structure of acetabular shells on the market today or may be on the market in the future. For example, some acetabular shells may comprise screw holes for anchoring the shell into the acetabulum. An appropriate embodiment of the engaging head consistent with Applicant's disclosure may be able to engage that shell as described herein.

Once the shell-engaging head 18 has been installed on the impactor 10 by an engagement with the coupler end 14, it may then be used to position and impact the acetabular shell 62 into the acetabulum of a patient at the appropriate time. The acetabular shell 62 may be held onto the shell-engaging head 18 by a subatmospheric pressure formed in the hollow passage 54. In one embodiment, the subatmospheric pressure may be formed by placing the acetabular shell over the tip portion 34 of the shell-engaging head 18. The resilient member 36 on the outer surface 37 may airtightly seal an enclosed region defined by the outer surface 37 and an inner surface of the acetabular shell. It will be appreciated that at this point, the hollow passage 54 may have only one other egress, the port 42. The surgeon then may place his or her thumb over the port 42 located on the head 16.

When the port 42 is initially sealed by the surgeon, the hollow passage 54 is substantially airtight and it will be observed that the air pressure inside of the hollow passage 54 may be equalized with the atmospheric pressure for a brief period of time. Due to the configuration of the shell-engaging head 18, a subatmospheric pressure may be formed when the acetabular shell attempts to move away from the shell-engaging head 18, or vice versa. This may be due to that fact that no outside air can enter the hollow passage 54 while the volume of the airtight region is being increased. It will be understood that as used herein, reference to movement of a portion of the impactor assembly 8 with respect to the shell or implant includes situations in which the implant remains stationary and the impactor assembly 8 moves, or situations in which the implant moves and the impactor assembly 8 remains stationary, or situations in which both the implant and the impactor assembly 8 move with respect to each other.

It will be appreciated that the movement of the shell away from the shell-engaging head 18 may be unobservable to the human eye. Once the subatmospheric pressure has been formed, the surgeon can then properly position the acetabular shell in the acetabulum using principles and techniques that are well known in the art and will not be recited here. Once the acetabular shell is in the correct position, the thumb may be removed from the port 42 and the pressure inside of the hollow passage 54 may again equalized with atmospheric pressure thereby releasing the acetabular shell. A surgical mallet may then be used to implant the shell into the acetabulum by striking the head 16 of the impactor 10.

It will be observed that the prior art is devoid of acetabular shell impactors utilizing a subatmospheric pressure to hold an implant without moving parts. Moreover, the prior art only teaches the use of an external suction source having a permanently fixed engaging head. In particular, it is observed that the Amstutz patent does not teach or suggest that a subatmospheric pressure may be formed by the interaction of the engaging head and the implant, i.e., the movement of the engaging head away from the implant.

Figure 8B:
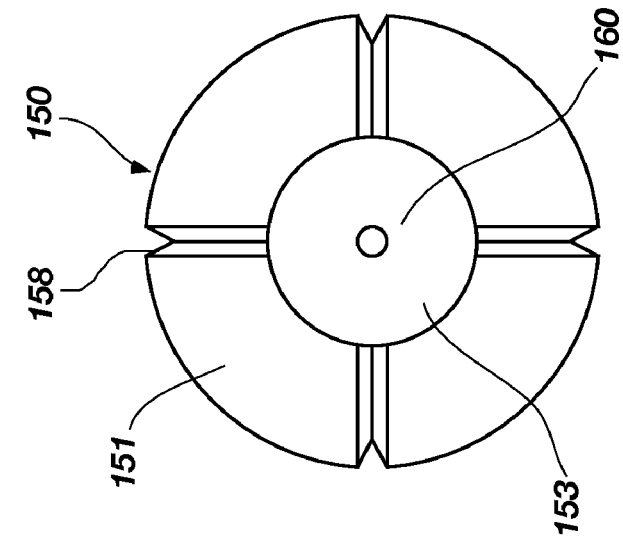
FIG. 8B is a top view of the liner-engaging head made in accordance with the present disclosure.
Figure 8A:
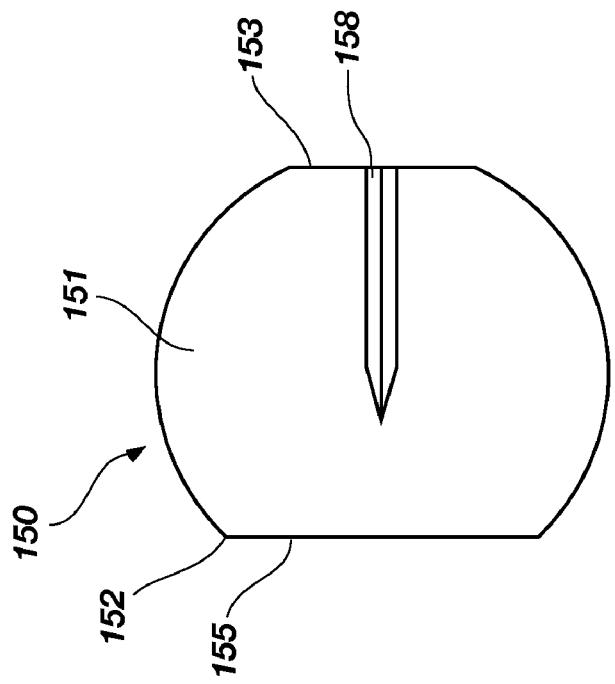
FIG. 8A is a side view of an exemplary embodiment of a liner-engaging head made in accordance with the present disclosure made in accordance with the present disclosure.
Figure 8C:
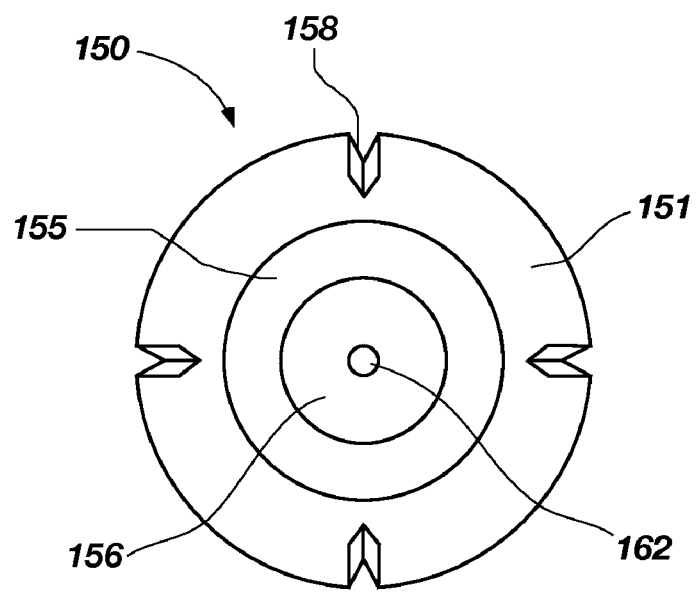
FIG. 8C is a bottom view of the liner-engaging head made in accordance with the present disclosure.

A side view, top view, a rear view of a liner-engaging head 150 are shown in FIGS. 8A, 8B, and 8C respectively. The liner-engaging head 150 may be used to install a socket liner 157 (see FIG. 9) into an implanted acetabular shell using the impactor 10 by engaging the socket portion of the socket liner 157. It will be appreciated that the socket liner 157 may be formed in various different sizes and configurations known in the art, and the liner-engaging head 150 may be configured to be compatible with the socket liner 157. The liner-engaging head 150 may comprise a tip portion 151 that may be partially spherical in shape. As mentioned, the tip portion 151 may be configured and sized to fit within the socket of the socket liner 157. The tip portion 151 may be resilient in nature to form a friction fit with the socket liner 157.

A base portion 152 of the liner-engaging head 150 may have a rearmost portion 155. Relief grooves 158 may extend from the forward most portion 153 towards the rearmost portion 155. In one embodiment, four relief grooves 158 may be used. However, it will be understood that any number of relief grooves 158 may be used within the scope of the present disclosure. A port 160 may be positioned in the forward most portion 153. A recessed portion 156 configured to engage the extension member 28 of the coupler end 14 may extend from the rearmost portion 155 towards the forward most portion 153. A port 162 may be located in the recessed portion 156.

Figure 9:
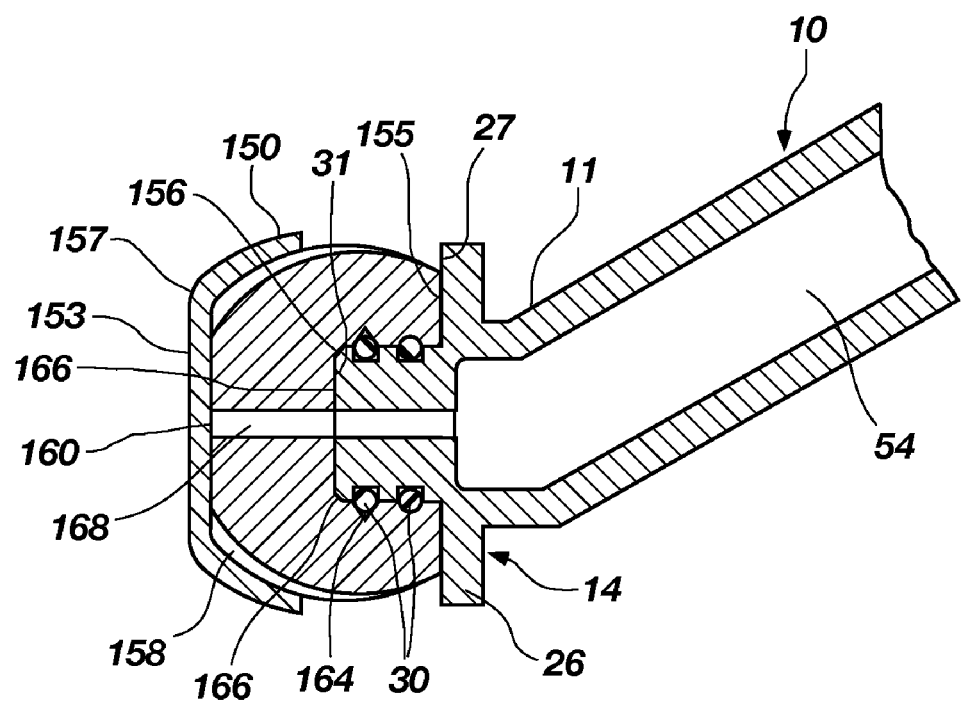
FIG. 9 is a cross-sectional side view of the liner-engaging head mounted on the impactor made in accordance with the present disclosure.

Looking now to a cross-sectional view of the engagement of the insert-engaging head 150 and the coupler end 14, the recessed portion 156 may slidably engage the extended member 28 as shown in FIG. 9. The forward most of the resilient members 30 on the extension member 28 may engage an annular locking grove 164 formed in a side wall 166 of the recessed portion 156 in order to form a friction fit to hold the insert-engaging member on the coupler end 14. The rearmost resilient member 30 on the extension member 28 may also engage the side wall 166 of the recessed portion 156 which a friction fit to hold the insert-engaging head 150 onto the coupler end 14.

The rearmost portion 155 of the base portion 152 may abut directly against the seat 27 of the annular flange 26 when the insert-engaging head 150 is installed on the coupler end 14. This interaction may serve to properly orient the insert-engaging head 150. Likewise, the exposed end 31 of the extension member 28 may abut against a bottom portion 166 of the recessed portion 156.

It will be observed that when the insert-engaging head 150 is properly installed onto the coupler end 14, that port 32 is in alignment and adjacent with port 162 such that port 160 is in direct fluid communication with the hollow passage 54. In this regard, the fluid communication path 33 may be interconnected with a fluid communication path 168 extending from port 160 to port 162.

Like the shell-engaging head 18, in the above described arrangement, the insert-engaging head 150 may be removed from the impactor 10 by using sufficient force to pull it off. It will be appreciated that the force to pull off the insert-engaging head 150 should be such that it can be done by an average strength human being as it may be necessary during surgery to replace the insert-engaging head 150.

After an acetabular shell has been implanted as described above, the surgeon may then remove the shell-engaging head 18 from the impactor 10 and install an appropriately sized liner-engaging head 150. The surgeon can then attach the socket liner 157 to the liner-engaging head 150 by inserting the tip portion 151 into the socket. The tip portion 151 may engage the socket by a friction fit. The socket liner 157 can then be positioned and implanted into the previously implanted acetabular shell. This may require an impaction force delivered to the head 16 by a surgical mallet. It will be appreciated that the head 16 may constitute a means for receiving an impaction force.

Once the socket liner 157 has been implanted into the shell, the socket liner 157 may then be disengaged from the liner-engaging head 150 so that the impactor 10 may be removed. The relief grooves 158 prevent and port 160 reduce the hydraulic suction that is sometimes generated between the liner-engaging head 150 and the socket liner when synorial fluid or another fluid is present. It will be appreciated that other embodiments of insert-engaging heads may be possible that fall within the scope of the present disclosure. Moreover, it will also be understood that another embodiment of the impactor 10 may be formed without the hollow passage 54 for use with the liner-engaging head 150.

It will also be appreciated that the base portions of the different engaging heads described above in their various embodiments, i.e. engaging heads and liner-engaging heads and their respective varying embodiments, may have a common configuration such that they may engage the same impactor. The common configuration allows engaging heads of different sizes and types to be used interchangeably on the same impactor. For example, different patients and circumstances may require different sized acetabular shells that may not be determined until during surgery. The common configuration of the engaging heads facilitates the process by providing a single impactor with a plurality of engaging heads and liner-engaging heads.

Figure 10:
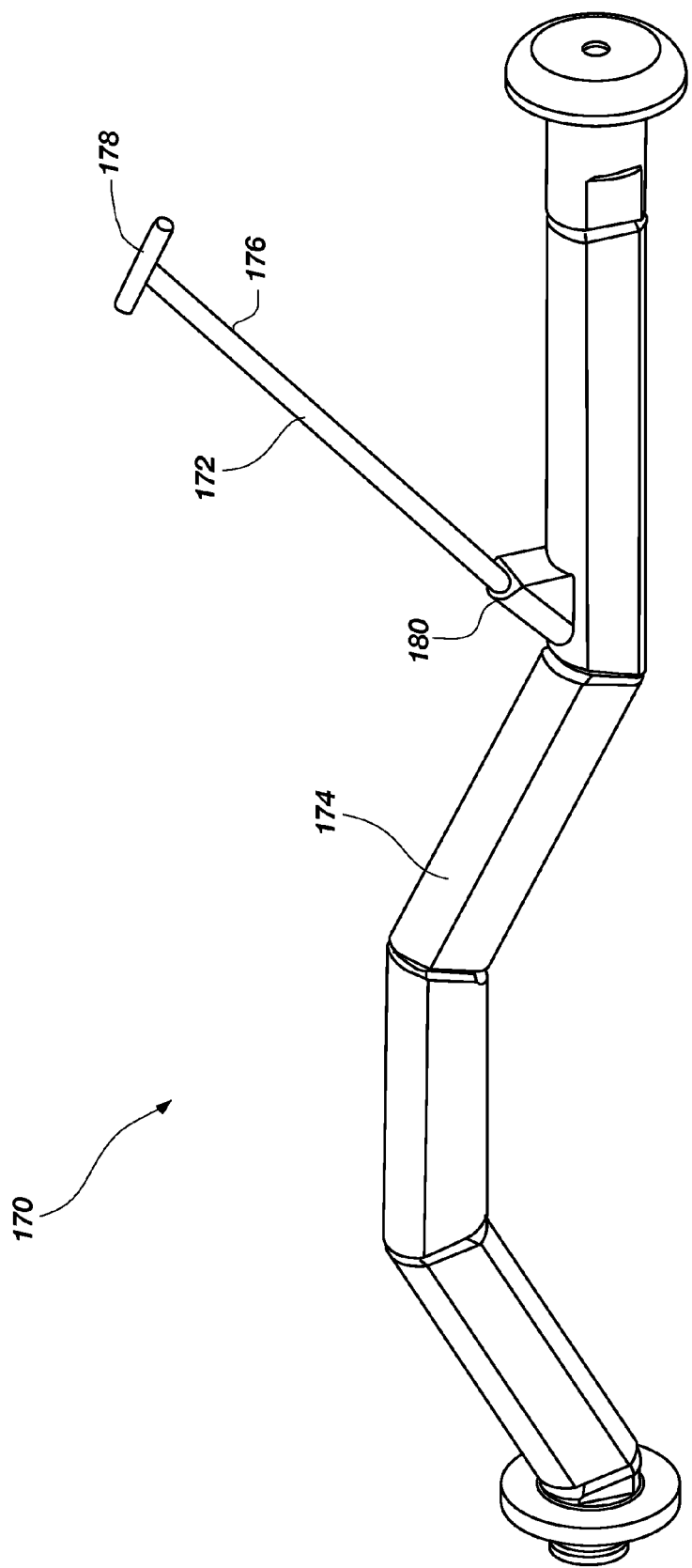
FIG. 10 is a perspective view of an exemplary embodiment of an impactor having a positioning handle made in accordance with the present disclosure.

FIG. 10 illustrates another embodiment of an impactor 170. An optional arm 172 may be coupled to an elongated body 174. The arm 172 may comprise an extended portion 176 and a handle 178. The arm 172 may be removably coupled by means of a threaded portion (not shown) on the end of the extended portion 176 that may rotatably engage a threaded bore 180 on the elongated body 174. The arm 172 may assist the surgeon in positioning the impactor 174 during surgery as is known in the art.

In accordance with the features and combinations described above, a useful method of implanting an acetabular shell may include the steps of:

(a) incising a hip with a minimally invasive incision to expose the acetabulum;

(b) preparing the acetabulum;

(c) providing an impactor having an elongate body, a head and a coupler end, the elongate body further comprising a bent portion and a hollow passage;

(d) installing an engaging head onto the coupler end;

(e) securing an acetabular shell to the engaging head by a subatmospheric pressure;

(f) positioning the shell into the acetabulum; and (g) applying an impaction force to the head in order to implant the shell into the acetabulum.

It will be understood that the structure disclosed herein may form one embodiment of a means for removably attaching an engaging head to an elongate body in a pressure-maintaining manner, such that any one of a plurality of engaging heads can be attached to the elongate body for installing surgical implants of different sizes. It should be appreciated that any structure, apparatus or system for removably attaching an engaging head which performs functions the same as, or equivalent to, those disclosed herein are intended to fall within the scope of a means for removably attaching an engaging head in a pressure-maintaining manner, including those structures, apparatus or systems for removably attaching an engaging head which are presently known, or which may become available in the future. Anything which functions the same as, or equivalently to, a means for removably attaching an engaging head in a pressure-maintaining manner falls within the scope of this element.

It will be appreciated that the elongate body 12 having a bent portion as disclosed herein is merely one example of a means for positioning an acetabular shell through a minimally invasive incision, and it should be appreciated that any structure, apparatus or system for positioning an acetabular shell through a minimally invasive incision which performs functions the same as, or equivalent to, those disclosed herein are intended to fall within the scope of a means for positioning an acetabular shell through a minimally invasive incision, including those structures, apparatus or systems for positioning an acetabular shell through a minimally invasive incision which are presently known, or which may become available in the future. Anything which functions the same as, or equivalently to, a means for positioning an acetabular shell through a minimally invasive incision falls within the scope of this element.

It will be appreciated that the head 16 disclosed herein is merely one example of a means for receiving an impaction force, and it should be appreciated that any structure, apparatus or system for receiving an impaction force which performs functions the same as, or equivalent to, those disclosed herein are intended to fall within the scope of a means for receiving an impaction force, including those structures, apparatus or systems for receiving an impaction force which are presently known, or which may become available in the future. Anything which functions the same as, or equivalently to, a means for receiving an impaction force falls within the scope of this element.

It will be appreciated that the coupler end 14 as disclosed herein is merely one example of a means for selectively engaging an engaging head by a pressure-maintaining seal, and it should be appreciated that any structure, apparatus or system for selectively engaging an engaging head by a pressure-maintaining seal which performs functions the same as, or equivalent to, those disclosed herein are intended to fall within the scope of a means for selectively engaging an engaging head by a pressure-maintaining seal, including those structures, apparatus or systems for selectively engaging an engaging head by a pressure-maintaining seal which are presently known, or which may become available in the future. Anything which functions the same as, or equivalently to, a means for selectively engaging an engaging head by a pressure-maintaining seal falls within the scope of this element.

It will be appreciated that the hollow passage 54 disclosed herein is merely one example of a means for forming a subatmospheric pressure, and it should be appreciated that any structure, apparatus or system for forming a subatmospheric pressure which performs functions the same as, or equivalent to, those disclosed herein are intended to fall within the scope of a means for forming a subatmospheric pressure, including those structures, apparatus or systems for forming a subatmospheric pressure which are presently known, or which may become available in the future. Anything which functions the same as, or equivalently to, a means for forming a subatmospheric pressure falls within the scope of this element.

It will be appreciated that the port 42 herein is merely one example of a means for breaking a subatmospheric pressure, and it should be appreciated that any structure, apparatus or system for breaking a subatmospheric pressure which performs functions the same as, or equivalent to, those disclosed herein are intended to fall within the scope of a means for breaking a subatmospheric pressure, including those structures, apparatus or systems for breaking a subatmospheric pressure which are presently known, or which may become available in the future. Anything which functions the same as, or equivalently to, a means for breaking a subatmospheric pressure falls within the scope of this element.

Those having ordinary skill in the relevant art will appreciate the advantages provide by the features of the present disclosure. For example, it is a feature of the present disclosure to provide an acetabular shell impactor with no moving parts. Another feature of the present disclosure to provide an acetabular shell impactor that utilizes a production of subatmospheric pressure to hold the acetabular shell on an engaging head of the impactor, without the need for an external subatmospheric pressure producing source. It is a further feature of the present disclosure, in accordance with one aspect thereof, to provide an acetabular shell impactor having interchangeable engaging heads to facilitate a hip replacement surgery. It is still another feature of the present disclosure to provide an acetabular shell impactor having interchangeable engaging heads and interchangeable liner-engaging heads.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An apparatus for installing an implant having a concave interior portion in a patient during surgery, said apparatus comprising:
    an elongate body comprising a hollow passage, a proximal end, and a distal end wherein the proximal end comprises an impact head, such that the elongate body is configured and arranged to serve simultaneously as a fluid communication channel and an impact-conveying body;
    an engaging head, having an engaging surface which is substantially partially spherical and convex, wherein the engaging surface has an annular groove, a resilient member being disposed in the annular groove and protruding outwardly from the annular groove and above the engaging surface, wherein the engaging head is disposed on the distal end of said elongate body, the resilient member of said engaging head configured to receive the concave interior portion of the implant in a pressure-maintaining seal formed partially at said resilient member, said engaging head and interior portion being configured to define an enclosed region when said implant is mated with said engaging head; and
    a fluid communication path interconnecting the enclosed region and the hollow passage;
    wherein said apparatus and all of its components are characterized by an absence of moving parts.

2. The apparatus of claim 1, further comprising a valveless and open port for selectively breaking a subatmospheric pressure formed in the hollow passage thereby permitting the implant to be selectively released from the engaging head; wherein said valveless and open port is characterized by an absence of mechanical parts connected to it.

3. The apparatus of claim 1, wherein there is no direct or indirect fluid communication path between the hollow passage and an external suction source.

4. The apparatus of claim 1, wherein the elongate body further comprises a bent portion adjacent to the distal end, said hollow passage extending from about the distal end to beyond the bent portion.

5. The apparatus of claim 4, wherein the bent portion is adapted to at least partially fit into a minimally invasive incision.

6. The apparatus of claim 1, further comprising a head disposed on the proximal end, said head comprising a top surface for receiving blows to install the implant.

7. The apparatus of claim 6, wherein the top surface is planar, and said top surface further comprises a port in fluid communication with said hollow passage for selectively breaking a subatmospheric pressure formed in the enclosed region thereby permitting the implant to be selectively released from the engaging head.

8. The apparatus of claim 1, further comprising a head disposed on the proximal end of the elongate body, wherein a port is formed in either the head or the elongate body, said port being valveless and open.

9. The apparatus of claim 8, wherein an imaginary longitudinal axis passes through a center of both the port and the fluid communication path.

10. The apparatus of claim 8, wherein the port is configured such that it may be sealed with a part of a human body.

11. The apparatus of claim 1, wherein the engaging head further comprises a substantially partially spherical portion having an outer surface having an annular groove, a resilient member being located in the annular groove.

12. The apparatus of claim 1, wherein the engaging head is interchangeable with any one of a plurality of engaging heads.

13. The apparatus of claim 1, wherein the elongate body further comprises a bent portion adjacent to the distal end, said hollow passage extending from about the distal end to beyond the bent portion, and the apparatus further comprises:
a head disposed on the proximal end, said head comprising a top planar surface for receiving blows for installing the implant into the patient; and
a port in fluid communication with said hollow passage for selectively breaking a subatmospheric pressure formed in the hollow passage thereby permitting the implant to be selectively released from the engaging head, the port disposed on the top planar surface.

14. The apparatus of claim 13, wherein the port is valveless and open.

15. The apparatus of claim 13, wherein the engaging head is interchangeable with any one of a plurality of engaging heads.

16. An apparatus for installing implants into a patient during surgery, each of the implants having a concave interior portion, the apparatus comprising:
an elongate body comprising a proximal end and a distal end;
a plurality of engaging heads, each engaging head having an engaging surface which is substantially partially spherical and convex, the engaging surface having a resilient member protruding outwardly and above the engaging surface, the resilient member configured to receive the concave interior portion of the implant in a pressure-maintaining seal formed partially at said resilient member;
a coupler end disposed on the distal end of the elongate body, said coupler end being configured to removably attach any one of the plurality of engaging heads by a pressure-maintaining seal; and
a port for selectively breaking a subatmospheric pressure formed in the elongate body thereby permitting implants to be selectively released from the engaging heads;
wherein an engaging head removably attached to the coupler end is interchangeable with any one of the other plurality of engaging heads such that implants of varying sizes and types may be installed with the apparatus.

17. The apparatus of claim 16, wherein the elongate body further comprises a bent portion, the bent portion being adapted to at least partially fit into a minimally invasive incision.

18. The apparatus of claim 17, wherein the elongate body further comprises a straight portion adjacent to the bent portion.

19. The apparatus of claim 16, further comprising a fluid communication path to an external suction source to thereby form a subatmospheric pressure.

20. The apparatus of claim 16, wherein the coupler end is configured to rotatably engage any one of the plurality of engaging heads.

21. The apparatus of claim 16, wherein the coupler end is configured to engage any one of the plurality of engaging heads by a snap fit.

22. The apparatus of claim 16, wherein the coupler end comprises an annular flange extending radially from a longitudinal axis, said annular flange forming a seat against which a base portion of each of the engaging heads may be configured to be positioned.

23. The apparatus of claim 22, wherein the coupler end further comprises a cylindrical extended portion extending along the longitudinal axis and away from the proximal end, said cylindrical extended portion adapted to slidably engage a recess in the base portion of each of the engaging heads.

24. The apparatus of claim 23, wherein the cylindrical extended portion further comprises an outer surface and an end surface, said outer surface comprising at least a first annular groove adapted to receive a first o-ring for forming the pressure-maintaining seal with an inner side wall of the recess in each of the engaging heads.

25. The apparatus of claim 24, wherein the inner side wall of the recess in each of the engaging head comprises a locking groove, said first o-ring engaging the locking groove to thereby at least partially secure an engaging head onto the coupler end.

26. The apparatus of claim 16, wherein each of the plurality of engaging heads further comprises a tip portion having an outer surface, a first annular groove being formed in the outer surface, a first o-ring being disposed in the first annular groove to thereby form a pressure-maintaining seal with the implant.

27. The apparatus of claim 26, wherein the tip portion comprises a substantially partially spherical shape.

28. The apparatus of claim 27, wherein the outer surface of the tip portion further comprises a port in fluid communication with a hollow passage in the elongate body.

29. An apparatus for installing surgical implants, said apparatus comprising:
an elongate body comprising a hollow passage, a proximal end, and a distal end;
a plurality of engaging heads each comprising a tip portion and a base portion, wherein the base portion of each of the engaging heads has a common configuration and the tip portion of each of the engaging heads has a first port;
the plurality of engaging heads comprising a first engaging head and a second engaging head, the tip portion of the first engaging head being configured to temporarily engage a first surgical implant and the tip portion of the second engaging head being configured to temporarily engage a second surgical implant;
a coupler end disposed at the distal end, the coupler end comprising a fluid communication path connected to the hollow passage of the elongate body; and
a port in fluid communication with said hollow passage for selectively breaking a subatmospheric pressure formed in the elongate body thereby permitting implants to be selectively released from the engaging heads;
wherein said coupler end is adapted to selectively engage said base portion of any of said engaging heads in a pressure maintaining seal to thereby fluidly interconnect the hollow passage and the first port of that engaging head engaged on the coupler end.

30. The apparatus of claim 29, wherein the first surgical implant is an acetabular shell and the second surgical implant is a socket liner.

31. The apparatus of claim 29, wherein the elongate body further comprises a bent portion, the bent portion being adapted to at least partially fit into a minimally invasive incision.

32. The apparatus of claim 29, wherein the first and second surgical implants are acetabular shells of different sizes.

33. The apparatus of claim 29, further comprising a head disposed on the proximal end, said head comprising a top planar surface.

34. The apparatus of claim 29, wherein the engagement of the coupler end and any of the plurality of engaging heads forms a pressure-maintaining seal.

35. The apparatus of claim 29, wherein the coupler end comprises an annular flange extending radially from a longitudinal axis, said annular flange forming a seat against which a base portion of an engaging head may be oriented.

36. The apparatus of claim 35, wherein the coupler end further comprises a cylindrical extended portion extending along the longitudinal axis and away from the distal end, said cylindrical extended portion adapted to engage a recess in the base portion of an engaging head.

37. The apparatus of claim 36, wherein the cylindrical extended portion further comprises an outer surface and an end surface, said outer surface comprising at least a first annular groove adapted to receive a first o-ring for engaging an inner side wall of the recess in an engaging head installed on the coupler end.

38. The apparatus of claim 37, wherein the inner side wall of the recess comprises a locking groove, said first o-ring engaging the locking groove to thereby at least partially secure an engaging head installed on the coupler end.

39. The apparatus of claim 29, wherein the tip portion of the first engaging head comprises a partially spherical portion having an outer surface, a first annular groove being formed in the outer surface having a first o-ring positioned therein.

40. The apparatus of claim 29, wherein the tip of the second engaging head comprises a partially spherical portion and a recess for engaging the coupler end.

41. The apparatus of claim 29, wherein the engaging heads rotatably engage the coupler end.

42. An apparatus for installing an implant having a concave interior portion in a patient during surgery, said apparatus comprising:
   an elongate body comprising a hollow passage, a proximal end, and a distal end;
   an engaging head, having an engaging surface which is substantially partially spherical and convex, wherein the engaging surface has an annular groove, a resilient member being disposed in the annular groove and protruding outwardly from the annular groove and above the engaging surface, wherein the engaging head is disposed on the distal end of said elongate body, the resilient member of said engaging head configured to receive an the concave interior portion of the implant in a pressure-maintaining seal formed partially at said resilient member, said engaging head and interior portion being configured to define an enclosed region when said implant is mated with said engaging head; and
   a fluid communication path interconnecting the enclosed region and the hollow passage;
   wherein said apparatus and all of its components are characterized by an absence of moving parts.

43. An apparatus for installing an implant in a patient during surgery, said apparatus comprising:
   an elongate body comprising a hollow passage, a proximal end, and a distal end wherein the proximal end comprises an impact head, such that the elongate body is configured and arranged to serve simultaneously as a fluid communication channel and an impact-conveying body;
   an engaging head having an engaging surface, wherein the engaging surface has an annular groove, a resilient member being disposed in the annular groove and protruding outwardly from the annular groove and above the engaging surface, wherein the engaging head is disposed on the distal end of said elongate body, the resilient member of said engaging head configured to receive an the concave interior portion of the implant in a pressure-maintaining seal formed partially at said resilient member, said engaging head and interior portion being configured to define an enclosed region when said implant is mated with said engaging head; and
   a fluid communication path interconnecting the enclosed region and the hollow passage;
   wherein said apparatus and all of its components are characterized by an absence of moving parts.

* * * * *